United States Patent [19]

Mazzilli

[11] Patent Number: 5,523,057
[45] Date of Patent: Jun. 4, 1996

[54] AIR STERILIZATION AND FILTERATION APPARATUS

[76] Inventor: Matt Mazzilli, 3397 SW. 42nd Ave., Palm City, Fla. 34990

[21] Appl. No.: 422,361

[22] Filed: Feb. 6, 1995

[51] Int. Cl.$^6$ .................................................. A61L 9/20
[52] U.S. Cl. ...................... 422/121; 422/122; 422/105; 55/279; 250/436
[58] Field of Search ..................... 422/4, 24, 121, 422/122, 105, 108; 250/432 R, 435, 438, 436; 55/279; 96/134

[56] References Cited

U.S. PATENT DOCUMENTS

| | | | |
|---|---|---|---|
| 2,628,083 | 2/1953 | Rense | 422/24 |
| 3,674,421 | 7/1972 | Decupper | 422/24 |
| 3,744,216 | 7/1973 | Halloran | 55/524 |
| 3,745,750 | 7/1973 | Arff | 422/24 |
| 3,750,370 | 8/1973 | Brauss et al. | 422/24 |
| 4,210,429 | 7/1980 | Golstein | 422/24 |
| 4,492,079 | 1/1985 | Takagi et al. | 60/274 |
| 4,990,313 | 2/1991 | Pacosz | 422/121 |
| 5,015,442 | 5/1991 | Hirai | 422/121 |
| 5,131,932 | 7/1992 | Glucksman | 55/274 |
| 5,145,496 | 9/1992 | Mellen | 55/188 |
| 5,185,015 | 2/1993 | Searle | 55/524 |
| 5,225,167 | 7/1993 | Wetzel | 422/121 |
| 5,417,729 | 3/1995 | Greenleaf, Sr. | 55/350.1 |

FOREIGN PATENT DOCUMENTS 0147217  8/1985  Japan .......................................... 422/4

*Primary Examiner*—Robert J. Warden
*Assistant Examiner*—Theresa T. Snider
*Attorney, Agent, or Firm*—McHale & Slavin

[57] ABSTRACT

The instant invention is a filtration system for use in residential and commercial buildings. The filtration apparatus consists of a galvanized steel for support of a tactified filter followed by a 254 nm ultraviolet light with the sterilized air then passed through an activated carbon filter for removal of chemical vapors. The filtration apparatus works in conjunction with a remotely located power supply pack which includes an air pressure activator so as to allow operation of the ultraviolet lights only when air movement is detected in a ventilation system. Installation of the device is compact, allowing placement in residential locations in conventional heater and air conditioning systems.

13 Claims, 1 Drawing Sheet

AIR STERILIZATION AND FILTERATION APPARATUS

FIELD OF THE INVENTION

This invention relates to ventilation systems and more particularly to a compact air sterilization and filtration apparatus for use with conventional ventilation systems found in residential and commercial properties.

BACKGROUND OF THE INVENTION

Conventional heating and air conditioning ventilation systems employ primary particle filters to prevent airborne debris from entering the system. Large particles such as leaves, dirt, hair, and rug lint, are ideally stopped by the filter to prevent interfering with the operation of the system. Excessive debris creates a fire hazard, for a heater operates at a temperature sufficient to start combustion.

The aforementioned filters are designed only to prevent large debris from entering the heater system. Particles as large as dust are not inhibited from a conventional filter. This phenomenon is evident when a heater is used infrequently. When the heater is started after a period of non-use, the heater burns the dust leaving a pungent smell capable of setting off smoke detectors.

While particles may be an annoyance in a ventilation system, the distribution of particles is dangerous for a person having health related problems. For instance, airborne particles may cause an asthma attack; bacteria spores may cause an allergic reaction; or chemical vapors may result in a rash. While many vapors cannot be detected by human senses or even sensitive equipment, many such vapors can accumulate in a person. For example, carpeting may propagate formaldehyde, a known carcinogen that may not have a detectable accumulation effect for years.

While conventional ventilation systems of the prior art have used a filter in order to protect the actual heating and ventilation components, only recently has the art progressed to the point of filtering the air for the purpose of protecting the recipients of the ventilation.

One known filter used in ventilation systems is the HEPA or high efficiency particle arresting filters which are approximately 73% efficient at trapping particles larger than 0.3 micron particles and 95% efficient at trapping particles larger than one micron. The problem occurs in that a majority of bacteria range in the size from 0.4 to 5 microns and can be easily trapped by a filter wherein the filter operates as a breeding ground for additional bacteria which can be sloughed off into the ventilation system. Viruses are much smaller, ranging in size from approximately 0.003 to 0.06 microns and are easily passed through a conventional filter for distribution throughout the ventilation system. While a HEPA filter has certain advantages, it does not treat bacteria or vapors and is cost prohibitive for the average residential or commercial property. It is not practical to trap all particles wherein variations and substitutions for particle trapping form the prior art in an effort to lessen the bacteria growth and particle distribution throughout a system.

In many situations a conventional filter, even a HEPA filter, is an organism amplifier. It is not uncommon to find a filter that is wet when no other water is apparent, the moisture content being the advent of a bacterial slime. In many instances, even if filters are changed regularly it is not uncommon to find filters filled with penicillium spores. When the filter is changed, it is not uncommon for the spores to be released into the ventilation system. Despite the frequency of filter exchanges, many closed ventilation systems have led to what has been called a "sick building". These buildings are designed to prevent energy loss by restricting air leakage. This air restriction further traps moisture in such buildings including chemical vapors from various consumer products such as formaldehyde, carbon monoxide, tobacco smoke, ammonia and so forth. Bacteria accumulation produced by wet cooling coils aggravates the condition by providing a breeding ground for bacteria wherein the ventilation system recirculates the bacteria throughout the building. Sick buildings, whether they be residential or office buildings have symptomatic complaints from the occupants for a variety of symptoms including headaches, fatigue, infections, neurological and psychological disorders, irritability, forgetfulness, burning of the eyes and throat, and so forth, which do not fit the pattern of any particular illness and are difficult to trace to any specific source.

In an effort to address these problems, various patents address items for use with ventilation systems. U.S. Pat. No. 4,990,313 discloses an ultraviolet light placed in-line in an air return system mounted downstream of a cooling coil. The light is disclosed for destroying of bacteria accumulations yet does not address proper pre-filtration of bacteria laden air bypassing the effectiveness of the light. Further, the disclosure does not provide for control of vapors or removal of dead spores which creates additional harmful particles in and of themselves.

U.S. Pat. No. 5,225,167 discloses a room air sterilizer utilizing an ultraviolet light having a pre-filter mounted before the light followed by a HEPA filter. While the patent discloses the advantages of a pre-filter and post filter, the device fails to teach filtration that is efficient or affordable. Further, the system does not address the control of chemical vapors or the possibility of ozone production from the ultraviolet light.

U.S. Pat. No. 5,015,442 discloses a filter system with an ozone producing ultraviolet light followed by an ozone decomposing catalyzer to destroy excess ozone. The intentional generation of ozone gas in a confined area is not acceptable for residential or point of use.

U.S. Pat. No. 5,186,903 discloses an apparatus for treating indoor air. This invention is directed to air contamination found in commercial, industrial and residential structures. Used in conjunction with a HVAC System, the device purifies air as well as removes trace substances of chemicals used in the cleaning and maintenance of a building as well as other substances found in air tight buildings. This invention does not disclose the use of an ultraviolet light and relies upon a molecular catalytic cracking of heavy hydrocarbons by use of an electrified catalyst, such as ozone, for destruction of constituents before removal through a filter system.

U.S. Pat. No. 5,298,043 discloses a complicated filter system for smoke and polluted air relying upon a set of sprayers that wash and moisturize the air before reuse.

U.S. Pat. No. 4,604,110 discloses still another air filter element for use in removing odors from indoor air systems based upon a mixture of silica gel, activated carbon and a fungicide/biocide to prevent micro-organisms from growing on the bed of the activated carbon.

U.S. Pat. No. 4,682,992 discloses a substance used for coating of air filters in order to prevent or inhibit microorganisms from growing. This is not a filtration system but discloses a coating mechanism that would be used with air filter systems.

Thus, what is lacking in the art is an affordable filtration system for use within a conventional ventilation system capable of reducing or eliminating airborne particles, bacteria, and chemical vapors with a means for reducing the moisture content of the filters and made of materials to prohibit bacterial growth.

SUMMARY OF THE INVENTION

The instant invention is a multistage filtration apparatus adaptable to any residential or commercial heater/AC ventilation system. The apparatus consists of a tackified primary filter capable of trapping airborne debris and microscopic particles such as pollen, lint, dust and so forth. The tack prevents dislodgment of the particles, all of which are capable of concealing bacteria which renders prior art ultraviolet lamps ineffective.

Air is directed into a chamber constructed of galvanized steel support structure with aluminum reflective foil on non-metal items. The galvanized steel inhibits bacterial growth and resists the corrosive effects of ozone and the foil reflection on each side panel focuses the ultraviolet intensity. With proper removal of the airborne debris, germicidal lamps producing 254 nm are found sufficient for destruction of airborne bacteria. The lamps are juxtapositioned to the filter wherein the heat from the lamps eliminates the moisture within the chamber and filter allowing proper destruction of mildew, algae, fungus, viruses, spores, and the like health threatening germs, and eliminating the moisture in the filter prevents the bacteria from living in the filter. A sail or pressure switch completes a circuit when the ventilation system is made operational so as to initiate the operation of the germicidal lamp.

The air is sterilized in a sealed chamber before passing through an activated charcoal absorption filter which absorbs various vapors from household cleaners including, disinfectants, paints, pesticides, formaldehyde, and the like chemical vapors. In addition, the activated carbon filter operates to trap radiated bacteria spores so as to prevent distribution of the dead spores throughout the ventilation system. The device is made operational by use of a sail or pressure switch mounted within the ventilation duct work which will turn on the lamps should air flow be sufficient to indicate blower fan operation. Preferably, an air pressure switch is used, as shown in the detailed description of the preferred embodiment, wherein an air pressure sensor tube detects the presence of air movement to initiate operation of the lamps.

The instant invention is a compact filtration apparatus which can be inserted into existing homes without modification to the current installed heating and/or air conditioning systems. A panel access switch disengages electrical power to the lamps should the side panels of the apparatus be removed while in operation. A fiberglass hard board with aluminum foil facing the interior of the housing focuses light reflection to insure against condensation of temperature difference. A shaded plastic peep hole provides visual indication as to whether the lamps are operational without escape of the radiant light.

When used in conjunction with an air conditioning system that operates extensively such as in tropical areas or closed buildings, a post germicidal lamp is available for positioning down stream of the wet coil so as to affect destruction of bacteria that may accumulate from the wet coil. A female plug is available on the side of the apparatus to allow coupling the remote lamp without additional wiring.

An objective of the instant invention is to set forth a compact filtration system for use in residential applications capable of removing airborne particles and vapors and destroying airborne bacteria.

Another objective of the instant invention is to teach an affordable sterilization and filtration apparatus which can be installed in existing heating and air conditioning systems without extensive rework or point of use.

Still another objective of the instant invention is to teach an apparatus utilizing a 254 nm minimum sized ultraviolet lamp having aluminum reflective side walls to enhance the ability of the lamp with minimal electrical amperage draw.

Yet another objective is to teach materials of construction to inhibit bacterial growth and reduce moisture from the filters by placement of the lamps within close proximity of the filters to control humidity within the apparatus housing.

Another objective of the instant invention is to provide a means for determining operation of the germicidal lamp without viewing the ultraviolet ray and providing a safety disconnect should the housing be opened while the lamps are operational.

Other objectives and advantages of this invention will become apparent from the following description taken in conjunction with the accompanying drawings wherein are set forth by way of illustration and example certain embodiments of this invention. The drawings constitute a part of this specification and include exemplary embodiments of the present invention and illustrate various objects and features thereof.

DETAILED DESCRIPTION OF THE PREFERRED EMBODIMENT

Although the invention is described in terms of a specific embodiment, it will be readily apparent to those skilled in this art that various modifications, rearrangements and substitutions can be made without departing from the spirit of the invention. The scope of the invention is defined by the claims appended hereto.

Figure 1:
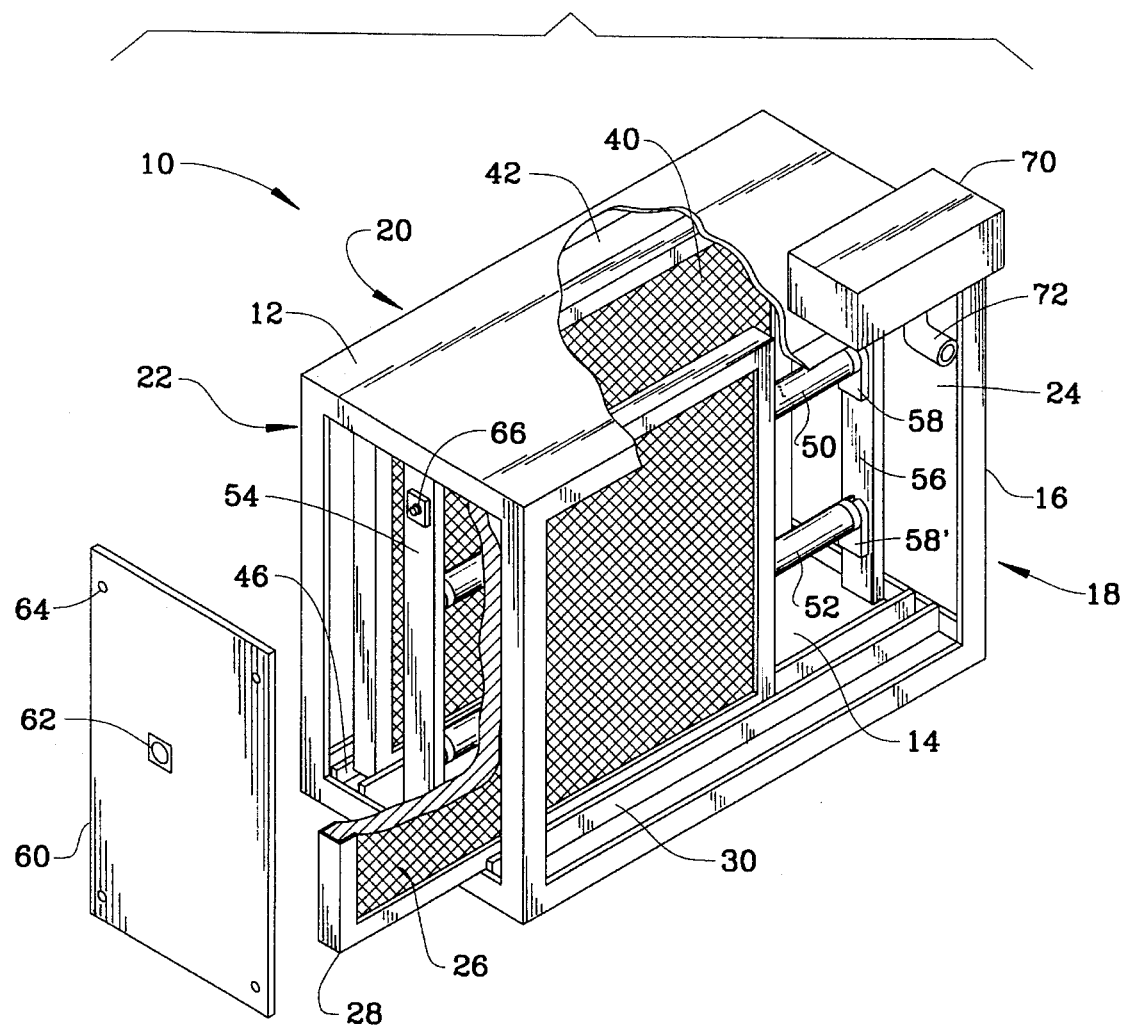
FIG. 1 is a perspective view of the filtration apparatus of the instant invention with a partial exploded view.
Figure 2:
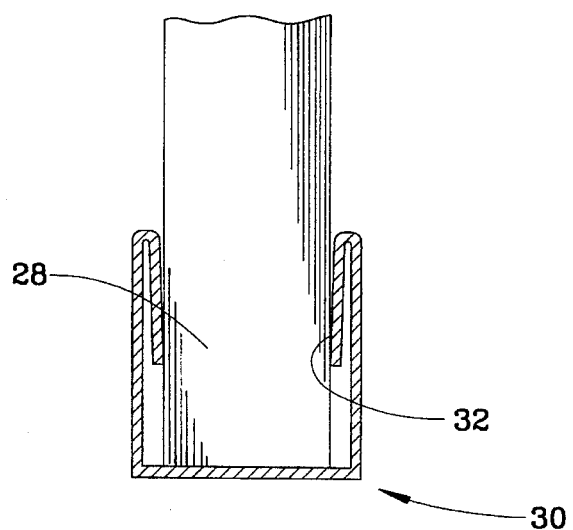
FIG. 2 is a side view of the filter support.

Now referring to FIG. 1 and 2 in general, illustrated is the preferred embodiment of the instant invention which is defined by a metal support structure 10 which houses the components of the filtration apparatus. The structure 10 has a rectangular shaped first plate 12 spaced apart from a second identical plate 14 along a corner edge of each plate 12 and 14 by spacer posts 16 of equal size defining an interior chamber with a first side opening 18 and a second side opening 20 with a first end opening 22 and second end opening 24. The preferred construction of the support structure 10 is galvanized metal as it has been found that the coating inhibits bacteria growth whereas plastic or the like semi-permeable material allows locations for growth of bacteria. The structure has a overall size of 20×20×12 inches.

A first filter means 26 is defined by a rectangular shaped outer periphery edge 28 supporting an air permeable filter material having a tackified surface. The filter traps particles such as dust, pollen, lint, hair and so forth using an air filter treated with a non-leaching tack. The tack prohibits dislodgment of the particles when a system is cycled, the change in air velocity typically dislodges particles in a conventional filter. The tactified filter prevents dislodgment of such particles and when the filter is exchanged, prevents dislodgment should the filter be upset.

The filter 26 is removably insertable through the first end opening 22 and positionable within said chamber in a juxtapose relation to the first side opening 18. A U-shaped filter runner 30 having a biased wall 32, provides frictional engagement to the periphery edge of the filters to prevent air from traveling about the edge of the filter. As described later in this specification, the end openings are sealed by a panel which further seals the filter in position eliminating the need for U-shaped runners when used with the proper filter design. It should be noted that undersized filters will require side panel sealing for proper operation of the apparatus. The objective for sealing the edge 28 of the filter 26 is to direct air through the first side opening 18 through the tactified filter material before entry into the interior chamber.

A second filter means 40 has a rectangular shaped outer periphery edge 42 supporting an air permeable filter material coated with activated carbon. The second filter means 40 is removably insertable through the first end opening 22 and positionable within said chamber in a juxtapose relation to the second side opening 20 and is parally spaced apart from the first filter 26 a predefined distance of approximately 12 inches. Similar to the first filter means, is a U-shaped filter runner 46 having a biased wall to provide frictional engagement to the periphery edge 42 of the filter 40 to prevent air from traveling about the edge of the filter. The objective for sealing the edge 42 of the filter 40 is to direct air leaving the chamber through the activated carbon filter. The second filter contains activated carbon impregnated sub-straits for removal of chemical vapors from the air as well as trappage of dead bacteria.

A first 50 and second 52 ultraviolet lamp is disposed within the chamber along the length of the structure extending from the first end opening 22 where each is attached to a first lamp frame leg to the second end opening 24 where each is attached to a second lamp frame leg and centrally disposed between the first filter 26 and second filter 40. Lamps 50 and 52 are mounted in fixtures 58 and 58' which are attached to support rails 54 and 56. Rail 54 vertically spans the center of opening 22 and rail 56 vertically spans the center of opening 24. The top and bottom ends of rails 54, 56 attach to upper plate 12 and lower plate 14 respectively. Central placement allows for the first lamp 50 to be spaced apart an equal distance from an inner surface of the first plate 12 and the second lamp 52. The second lamp 52 is spaced apart an equal distance from an inner surface of the plate 14 and the first lamp 50. Each ultraviolet lamp radiates at a wavelength of 254 nm providing germicidal destruction. Since a ultraviolet light can also produce ozone, the activated carbon is positioned for destruction of any ozone production. In this regards, a 185nm ozone producing ultraviolet lamp can be substituted for the germicidal lamp without further modification. The properties of activated carbon filter will prevent the passage and distribution of ozone into the ventilation system.

A first end wall 60 is sealably securable to the first end opening 22. The end wall 60 is rectangularly shaped and constructed of hardboard such as fiberglass or equivalent lightweight material having a layer of reflective foil on the inner surface of the wall to reflect and focus the radiant energy of the lamps into the chamber of the structure. An aperture 62 is provided for viewing lamp operation in each end wall with a plastic colored shield capable of filtering ultraviolet light.

The end wall 60 is secured to the structure by lock handles 64 to prevent unauthorized entry into the structure during lamp operation. Should an end wall be opened when electricity is operating the lamps, safety switch 66 which is depressed by the attachment of the end wall 60 is released into an open position which is coupled to a power supply operatively associated with the lamps for disconnecting power to the lamps.

The power to the germicidal lamps is provided through a remotely positioned power pack 70 which can be positioned within, or adjacent to, the ventilation duct. In this embodiment it is shown coupled directly to the structure for ease of illustration. The power pack 70 houses the ballast and transformer for the lamps in a separate location allowing the chamber to remain unobstructed by components providing a clear area for bacteria destruction and prohibit excess heat accumulation within the chamber. Placing the power pack 70 in or next to a ventilation duct provides for efficient heat distribution. An air pressure switch mounted in the power pack will sense pressure caused by air movement within a ventilation duct by insertion of pitot tube 72 causing power coupling to the lamps for proper operation. Alternatively, a two stage pressure switch is coupled to the power supply having a first stage for detection of air movement in a ventilation system providing automatic operation of the lamps when air pressure is detected and a second stage for detection of pressure differential across the first filter with an alarm such as a buzzer to indicate filter clogging. A sail switch, which is the term in the electrical industry describing a switch which is activated upon the application of airflow over the switch and is not shown, can also be coupled to the power supply for detection of air movement in a ventilation system providing automatic operation of said lamps when air movement is detected.

The support structure is sized to attach to a conventional air intake chamber on a residential heater/air conditioning system. Air entering the first primary filter is detected causing operation of the lamps 50 and 52 as the air entering the ultraviolet light chamber passes through the filter 26 for removal of airborne particles which are trapped by the tackified surface. The particles removed by the filter are capable of concealing airborne bacteria. The carbon filter traps the dead bacteria and chemical vapors by absorption.

In an alternative embodiment, the instant invention can be placed anywhere in a ventilation system such as the treatment of an individual's office in a commercial setting wherein the pressure switch will operate the system providing particle removal, bacteria destruction, and vapor removal upon demand when air is being delivered into an individual office. This further simplifies installation, for unique residential properties as an external source of operation need not be determined in each circumstance which can be quite complicated in light of the numerous types of installations possible accompanied by the numerous manufacturers of ventilation systems. For instance, the installation of the Applicant's invention in a condominium may not be possible directly at the ventilation system source, yet the resident may treat their individual unit having all the benefits of a full scale treatment system in a compact housing that can be positioned and operated anywhere in a length of ventilation duct work.

In a second embodiment of the instant invention a secondary ultraviolet light may be located downstream from a wet coil of an air conditioning system wherein the aforementioned invention provides a primary filtration before an air conditioning unit wherein filtered air is passed through the air conditioning unit where it comes in contact with a wet coil which is known to be a breeding ground of bacteria. For this reason, a secondary ultraviolet lamp can be located downstream from the ventilation system and wet coil to provide bacteria kill of particles picked up from the wet coil. The remote ultraviolet light is preferably supported by a U-shaped galvanized bracket for directing the light into the ventilation duct. A remote lamp can be coupled to the power pack by a multi-wire male plug which is receptive to a female receptacle located in the power pack allowing single power source operation.

It is to be understood that while I have illustrated and described a certain form of my invention, it is not to be limited to the specific form or arrangement of parts herein described and shown. It will be readily apparent to those skilled in the art that various changes may be made without departing from the scope of the invention and the invention is not to be considered limited to what is shown in the drawings and described in the specification.

What is claimed is:

1. Filtration apparatus for use in combination with a fixed heating/air conditioning ventilation system comprising: a support structure constructed of galvanized steel having a rectangular shaped first plate spaced apart from an identical second plate along a corner edge of each said plate by spacer posts of equal size defining an interior chamber with a first and second side opening and a first and second end opening; first filter means having a rectangular shaped outer periphery edge supporting an air permeable filter material having a tackified surface, said first filter means removably insertable through said first end opening and positionable within said chamber in a juxtapose relation to said first side opening, means for securing the edge of said first filter means to said chamber directing air engaging said first side opening through the tackified material; second filter means having a rectangular shaped outer periphery edge supporting an air permeable filter material coated with activated carbon, said second filter means removably insertable through said first end opening and positionable within said chamber in a juxtapose relation to said second side opening parallely spaced apart from said first filter means a predefined distance, means for securing the edge of said second filter means to said chamber directing air forced into said chamber though the activated carbon material; a first and second ultraviolet lamp each having a length extending from said first end opening to said second end opening centrally disposed between said first and second filter means, said first lamp spaced apart an equal distance from said first plate and said second lamp, said second lamp spaced apart an equal distance from said second plate and said first lamp; a first and second end wall sealably securable to said first and second end openings, each said end wall having a reflective inner surface and a means for viewing lamp operation; and a power supply operatively associated with said lamps; whereby said support structure attaches to a heater/air conditioning system wherein air directed through said first primary filter is stripped of airborne particles capable of concealing airborne bacteria and is then subjected to ultraviolet radiation from or ozone propagated by said lamps providing germicidal destruction of the bacteria before passing through said secondary filter means for removal of dead bacteria and chemical vapors.

2. The filtration apparatus according to claim 1 wherein said first and second plates are each approximately 12 inches wide and approximately 20 inches long.

3. The filtration apparatus according to claim 1 wherein an outer surface of said first plate is parallely disposed approximately 20 inches from an outer surface of said second plate.

4. The filtration apparatus according to claim 1 wherein said means for viewing lamp operation is further defined as an aperture placed through each said end wall having a plastic colored shield capable of filtering ultraviolet light.

5. The filtration apparatus according to claim 1 wherein said means for securing the edge of each said filter means is further defined as a U-shaped filter runner having a biased wall providing frictional engagement to said periphery edge of each said filter means.

6. The filtration apparatus according to claim 1 wherein each said ultraviolet lamp is capable of radiating at a wavelength of 254 nm providing germicidal destruction.

7. The filtration apparatus according to claim 1 including a switch means coupled to said power supply for detection of air movement in a ventilation system providing automatic operation of said lamps when air pressure is detected.

8. The filtration apparatus according to claim 7 wherein said switch means is further defined as a sail switch.

9. The filtration apparatus according to claim 7 wherein said switch means is further defined as a pressure switch.

10. The filtration apparatus according to claim 1 including a two stage pressure switch coupled to said power supply having a first stage for detection of air movement in a ventilation system providing automatic operation of said lamps when air pressure is detected and a second stage for detection of pressure differential across said first filter means having an alarm means to indicate filter clogging.

11. The filtration apparatus according to claim 1 wherein said structure is 20 inches wide by 20 inches long by 12 inches wide allowing replacement of influent filters having a ventilation system receptive to filters of industry standard.

12. The filtration apparatus according to claim 1 wherein each said ultraviolet lamp is capable of radiating at a wavelength of 185 nm providing ultraviolet light and ozone for germicidal destruction.

13. Filtration apparatus for use in combination with a fixed heating/air conditioning ventilation system comprising: a support structure constructed of galvanized steel having a rectangular shaped first plate spaced apart from an identical second plate along a corner edge of each said plate by spacer posts of equal size defining an interior chamber with a first and second side opening and a first and second end opening; first filter means having a rectangular shaped outer periphery edge supporting an air permeable filter material having a tackified surface, said first filter means removably insertable through said first end opening and positionable within said chamber in a juxtapose relation to said first side opening, means for securing the edge of said first filter means to said chamber directing air engaging said first side opening through the tackified material; second filter means having a rectangular shaped outer periphery edge supporting an air permeable filter material coated with activated carbon, said second filter means removably insertable through said first end opening and positionable within said chamber in a juxtapose relation to said second side opening parallely spaced apart from said first filter means a predefined distance, means for securing the edge of said second filter means to said chamber directing air forced into said chamber thought the activated carbon material; a first and second ultraviolet lamp each having a length extending from said first end opening to said second end opening centrally disposed between said first and second filter means, said first lamp spaced apart an equal distance from said first plate and said second lamp, said second lamp spaced apart an equal distance from said second plate and said first lamp; a first and second end wall sealably securable to said first and second end openings, each said end wall having a reflective inner surface and a means for viewing lamp operation; and a power supply operatively associated with said lamps having a means for detecting air movement to control operation of said lamps; whereby said support structure is sized to attach to a conventional air intake chamber on a residential heater/air conditioning system wherein air directed through said first primary filter is stripped of airborne particles capable of concealing airborne bacteria and is then subjected to ultraviolet radiation from or ozone propagated by said lamps providing germicidal destruction of the bacteria before passing through said secondary filter means for removal of dead bacteria and chemical vapors.

* * * * *